United States Patent [19]

Heyman

[11] Patent Number: 5,192,450
[45] Date of Patent: Mar. 9, 1993

[54] ACOUSTOPHORESIS SEPARATION METHOD

[75] Inventor: Joseph S. Heyman, Williamsburg, Va.

[73] Assignee: The United States of America as represented by the Administrator of the United States National Aeronautics and Space Administration, Washington, D.C.

[21] Appl. No.: 901,627

[22] Filed: Jun. 17, 1992

Related U.S. Application Data

[62] Division of Ser. No. 628,062, Dec. 17, 1990, Pat. No. 5,147,562.

[51] Int. Cl.$^5$ .............................................. B01D 17/06
[52] U.S. Cl. ..................................... 210/748; 55/277; 210/767; 210/806; 406/197
[58] Field of Search ............... 210/739, 748, 767, 806, 210/695; 55/277; 406/197, 198; 209/345, 427

[56] References Cited

U.S. PATENT DOCUMENTS 4,759,775  7/1988  Peterson et al. ...................... 210/748
4,877,516 10/1989  Schram ................................ 210/748
5,085,783  2/1992  Feke et al. ........................... 210/748
5,128,043  7/1992  Wildermuth .......................... 210/748

Primary Examiner—Robert A. Dawson
Assistant Examiner—Sun Uk Kim
Attorney, Agent, or Firm—Kevin B. Osborne

[57] ABSTRACT

A method and apparatus are provided for acoustophoresis, i.e., the separation of species via acoustic waves. An ultrasonic transducer applies an acoustic wave to one end of a sample container containing at least two species having different acoustic absorptions. The wave has a frequency tuned to or harmonized with the point of resonance of the species to be separated. This wave causes the species to be driven to an opposite end of the sample container for removal. A second ultrasonic transducer may be provided to apply a second, oppositely directed acoustic wave to prevent undesired streaming. In addition, a radio frequency tuned to the mechanical resonance and coupled with a magnetic field can serve to identify a species in a medium comprising species with similar absorption coefficients, whereby an acoustic wave having a frequency corresponding to this gyrational rate can then be applied to sweep the identified species to one end of the container for removal.

1 Claim, 4 Drawing Sheets

ACOUSTOPHORESIS SEPARATION METHOD

ORIGIN OF THE INVENTION

The invention described herein was made by an employee of the United States Government and may be manufactured and used by or for the Government for governmental purposes without the payment of any royalties thereon or therefor.

This is a divisional of copending application Ser. No. 07/628,062 filed on Dec. 17, 1990, now U.S. Pat. No. 5,147,562.

BACKGROUND OF THE INVENTION

1. Technical Field of the Invention

The invention relates to the field of chemical separation and more particularly to a method and apparatus for acoustophoresis, i.e., the separation of species via acoustic waves.

2. Description of the Related Art

Prior methods of species separation depend for the most part on gravity, with the separation depending on material density. Artificially high gravity gradients achieved by centrifuging can separate very small differences in density. Solubility, freezing, and boiling are also processes for separation, with each depending on a specific physical/chemical property to achieve the separation. Another process is electrophoresis, which produces a chemical separation based on the interaction of the species with an electric field. Each of these methods is unable to separate species with similar separation properties key for the particular method. Freezing and boiling separation may also damage the chemical or solid species or change their properties. In addition, high gravity techniques are expensive and rather complex.

Prior separation techniques involving acoustic or sonic energy have relied on either intense acoustic standing waves and associated migration or direct reflection related forces at planar interferences, not acoustic absorption or radiation pressure characteristics.

OBJECTS OF THE INVENTION

It is accordingly an object of the present invention to provide a method and apparatus to separate liquids or suspended solids based on such acoustic property absorption coefficients and mechanical resonance.

It is another object of the present invention to separate species having different acoustic properties.

It is a further object of the present invention to separate species having similar acoustic properties.

Other objects and advantages are apparent from the following specification.

SUMMARY OF THE INVENTION

The forgoing and additional objects are obtained by a method and apparatus for chemical separation based on acoustic absorption scattering and nonlinear properties according to the present invention. This method is hereinafter denoted as acoustophoresis.

An ultrasonic transducer applies an acoustic wave to one end of a sample container containing various species having different absorption coefficients. The frequency of this wave is tuned to or harmonized with the point of resonance of the species to be separated, whereby the species is moved toward an opposite end of the container for removal. A second transducer may be provided at this other end to direct a second acoustic wave having a different frequency and amplitude to prevent streaming of another species having acoustic properties similar to the species to be separated. If these properties are very similar, a radio frequency may be applied to the sample container to excite the dipolar field of the species to be separated. A magnetic field is then cross-coupled to the radio field to cause this species to rotate with a specific gyrotational rate, thereby "tagging" this species for an applied acoustic wave having a frequency corresponding to this gyration rate and which sweeps the species for removal.

This device provides a novel separation technique capable of differentiating species by their acoustic properties of acoustic absorption, scattering and radiation stress.

DETAILED DESCRIPTION OF THE INVENTION

Figure 1:
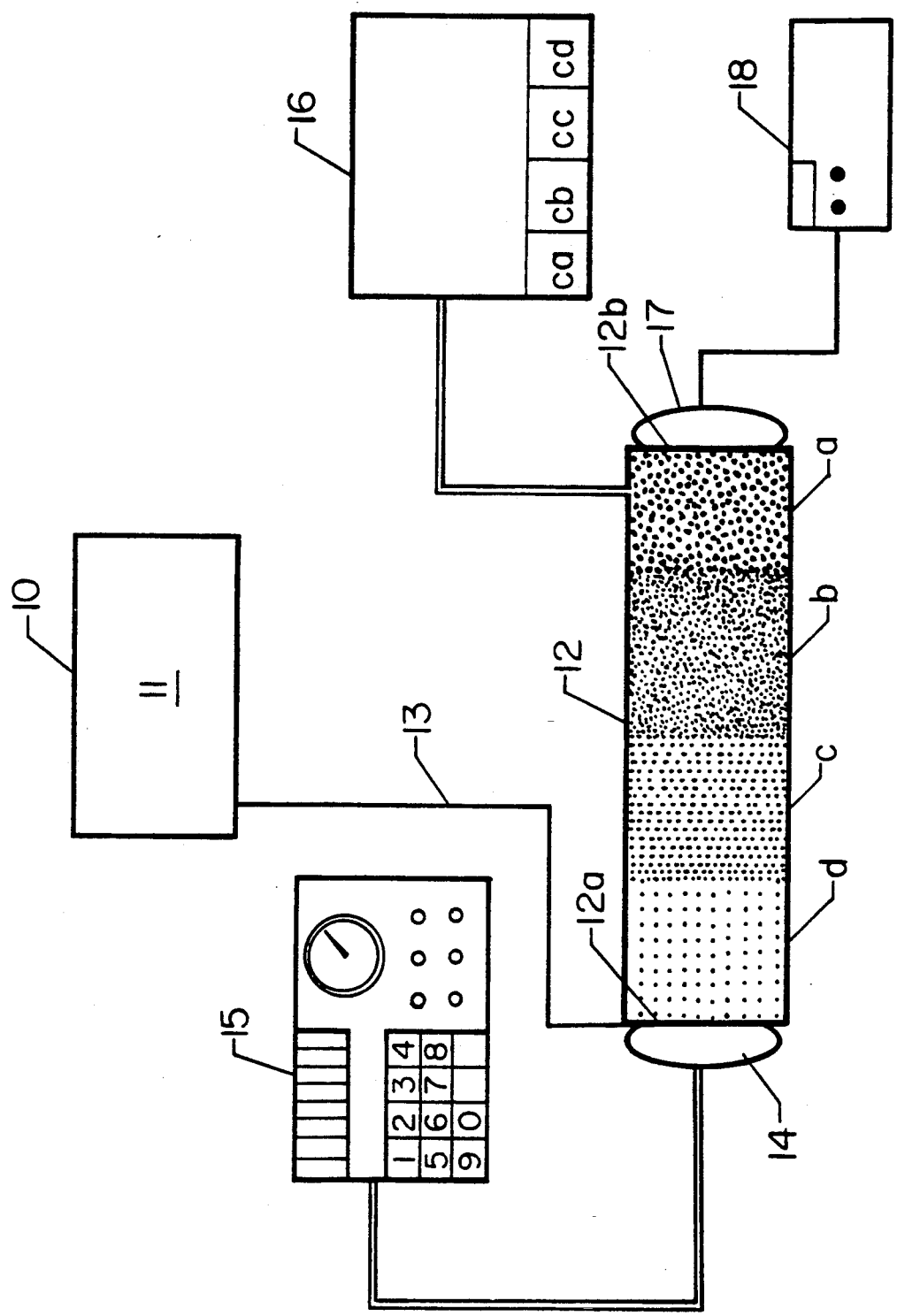
FIG. 1 is a block diagram of an acoustophoresis apparatus in accordance with a preferred embodiment of the invention.

The theoretical basis of the radiation pressure is discussed first. The radiation pressure $P_{rad}$ is given by:

$$P_{rad} = I_1[(1+R)/V_1 - (1-R)(1-\alpha)/V_2)] \quad (1)$$

where $I_1$ is the incident acoustic intensity equal to the power transmitted per second through a unit area in region 1, R is the reflection coefficient for intensities defined as:

$$R = \{(m-1)/m+1)\}^2 \text{ where } m = Z_2/Z_1 \text{ and } Z = \rho V, \quad (2)$$

$\rho$ is the density, V is the acoustic velocity, $\alpha$ is the acoustic absorption, and the subscripts 1, 2 refer to the initial and later medium, if different.

Equation (1) results in the following generalizations:

(a) if the wave is totally reflected by medium 2, then the radiation pressure is:

$$P_{rad} = 2I_1/V_1; \text{ or } P_{rad} = 2E_1, \text{ where E is the energy density } I/V; \quad (3)$$

(b) if the wave is totally absorbed by medium 2, then the radiation pressure is:

$$P_{rad} = I_1/V_1; \text{ or } P_{rad} = E_1; \text{ and} \quad (4)$$

(c) if there is zero reflection and absorption, then:

$$P_{rad} = I_1/V_1 - I_2/V_2; \text{ or } P_{rad} = E_1 - E_2, \quad (5)$$

the difference in energy density in the two regions. The energy per unit volume is:

$$E = \pi \omega \rho V \xi^2 \lambda \quad (6)$$

where $\omega$ is the acoustic frequency, $\rho$ is the density of the material, $\xi$ is the particle displacement, and $\lambda$ is the acoustic wavelength.

Any of the above parameters can alter the acoustic energy density. The energy density thus depends not only on the stimulus, but also on physical properties of the propagation material.

Figure 2:
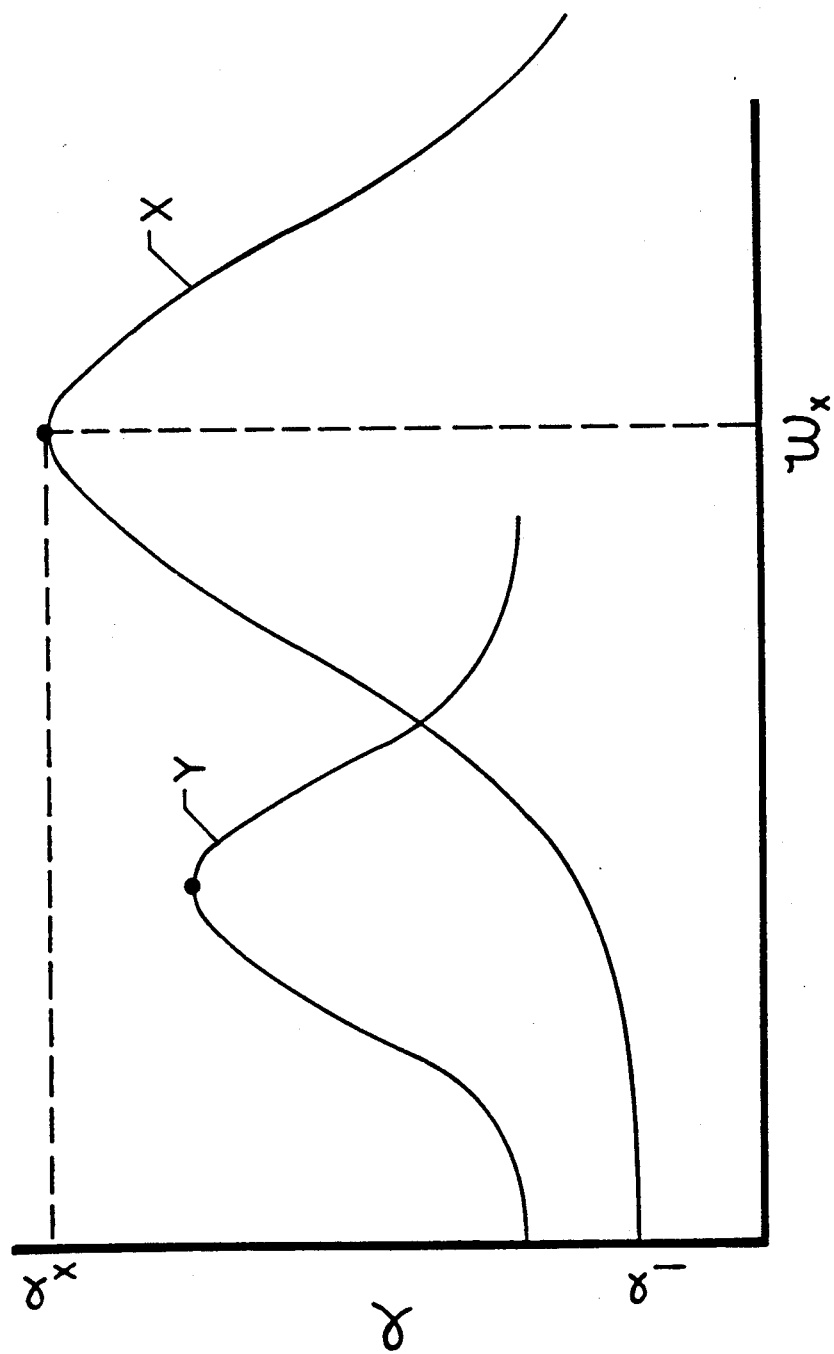
FIG. 2 is a graph showing the relationship between the acoustic absorption and the applied frequency for particular species.

The present invention uses acoustic physical properties as a separation mechanism and employs a differential separation process based on the frequency dependent propagation processes. As an ultrasonic wave passes through a medium, it carries energy and momentum. The loss of energy by the wave results in a transfer of momentum to the substance that absorbs the energy. For example, since molecular chains absorb ultrasonic energy through mechanisms such as resonance relaxation, the force on these chains depends on the frequency of the acoustics. Therefore, by selecting a specific frequency, one can "tune in" to a select physical property of the species, i.e., acoustic absorption, and separate chemical species with different acoustic absorption coefficients that may be impossible to separate by other means. This specific frequency is selected by tuning the frequency to the particular point of resonance $a_x$ of the species to be separated, as shown in FIG. 2 wherein curve X represents a relatively smaller species and curve Y represents a relatively larger species. When $a_x >> a_1$, the resulting radiation pressure $P_{rad}$ from the tuned frequency $\omega_x$ will move the species x since $\rho_x >> \rho_1$. The frequency of the acoustic wave can also be harmonized with the mechanical resonance.

For particulate separation, the choice of acoustic wavelength will change the acoustic scattering process and thus the force imparted to the suspended particles. As the frequency is increased in quantized increments from low to high, the large particles will scatter first, followed by the smaller particles. The larger suspended particles will be swept from the liquid first by the transferred momentum.

Turning now to FIG. 1 showing a preferred embodiment, a feed source 10 stores a quantity of a supply medium 11 to be separated, in this instance a suitable liquid comprising species having different absorption coefficients. Supply medium is fed into a separation sample container 12 through conduit 13. An ultrasonic transducer source 14 is located on a first wall 12a of container 12. This transducer source 14 is connected to an ultrasonic driver 15 which sends an ultrasonic wave into the supply medium 11, thereby producing a radiation drag on the various species in the liquid determined by their respective absorption of the acoustic wave. Those species with small absorption coefficients will experience a smaller force than the highly absorbent species. The resulting interaction of the species causes a separation of species based on the absorption or scattering of the acoustic wave. If the frequency of this wave is equal to or harmonized with the point of resonance of a species to be separated, then this species will be moved toward the opposing wall 12b.

The sequentially separated species a, b, c, d are removed by a pump separator 16 having respective storage compartments ca, cb, cc, cd which receive the respective separated species. The depicted location and number of the storage compartments in the pump mechanism is of course by way of example only and is a matter of design choice for the particular application. In addition, any conventional removal system or method may be employed. To prevent mixing, a separated species is removed and then a subsequent species separated and driven to the opposite wall 12b by changing the frequency of the acoustic wave to match the point of resonance of this subsequent species.

If the respective absorption coefficients of the differing species are nearly equal, then acoustic streaming may mix the liquid and therefore prevent separation by this method. To minimize this undesirable effect, a second transducer 17 is provided which is driven by an anti-streaming device 18 to produce a second acoustic wave. This second acoustic wave can be tuned to a different frequency and a different amplitude than the first wave to produce a high resolution "shearing" of the liquid into its separate species. This second acoustic wave serves to exert a counter-force in the direction of wall 12a against the second species which would otherwise be moved toward wall 12b along with the selected species moved by the first acoustic wave generated by the first transducer 14, whereby the second species is in effect braked.

The acoustophoresis concept can utilize not only bulk compressional waves, but also surface waves or boundary waves between a solid (or liquid) container wall and the subject liquid. The free surface of the subject liquid acts as a wave guide containing the input of acoustic energy.

Figure 3:
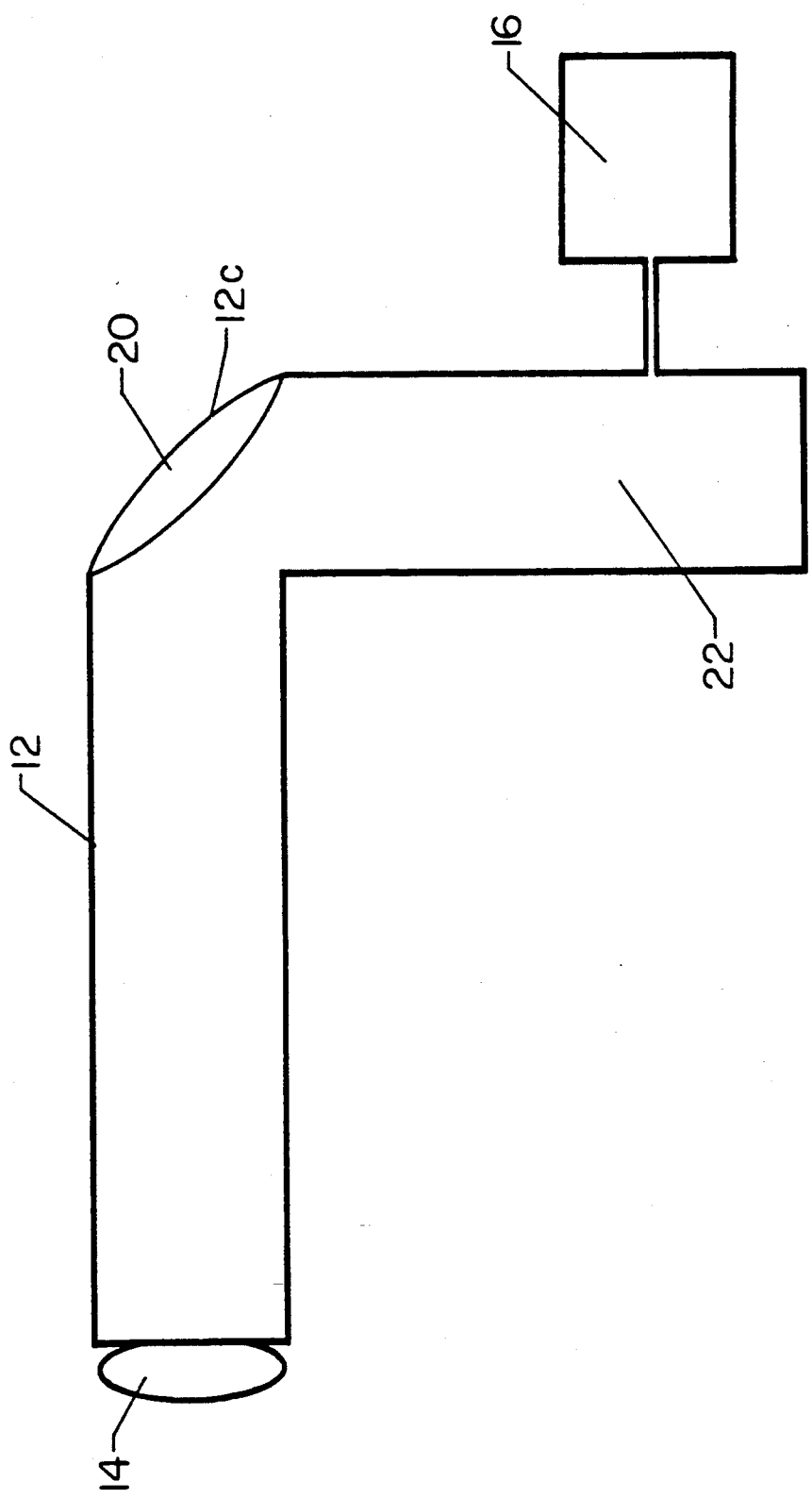
FIG. 3 is a block diagram of another embodiment of the present invention having a reflector and a settling chamber.

In a different embodiment of the device, the opposing wall 12b of the container 12 can be acoustically absorbing so as to prevent a backward propagating wave caused by excessive sound pressure. Also, as shown in FIG. 3, a reflector 20 may be located at angeled opposing wall 12c and set at an angle to the wave propagation direction, whereby the wave is reflected out of the sample chamber 12 into a settling chamber 22 to capture the separated species as well as the acoustic wave. The separated species is then removed by a pump separator 16 or by any other conventional method. Multiple reflectors and chambers may be employed so that a compact member is formed whereby the chambers are stacked one upon another to save space in the lengthwise direction, i.e., from wall 12a to 12c. For high viscosity liquids, shear acoustic waves may also be used for the driving energy.

Figure 4:
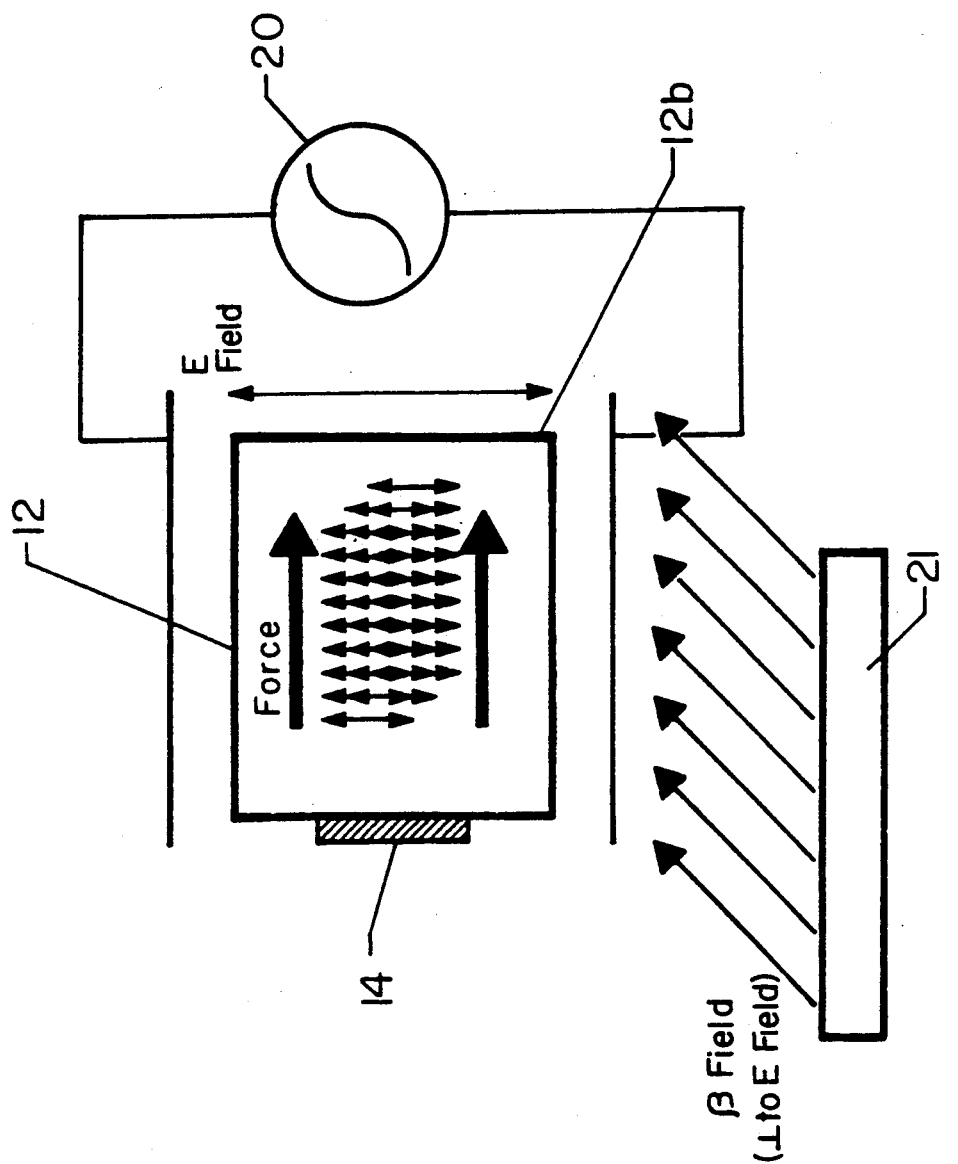
FIG. 4 illustrates the operation of a secondary coupling mechanism according to the present invention.

There are some applications of separation which require differentiation of specific molecular species beyond the innate acoustic properties of absorption or scattering, such as when the species have similar absorption coefficients. For these species, a mechanism of specificity is achieved by coupling energy to the species in question through externally applied fields as shown in FIG. 4.

For example, an alternating radio frequency (RF) field can be tuned to a mechanical resonance of the species to be separated via RF signal generator 20. This field will oscillate the dipolar field of the selected one of the molecular species. Next, a magnetic field is produced by conventional magnetic field generator 21 and is crossed or coupled perpendicularly with the RF field, causing the molecules of this selected species to spin at a specific gyrational rate. The net result is that the $q \cdot V \times \beta$ force, where q is charge, V is the velocity, and $\beta$ is the magnetic field, is tuned to a frequency accessible to the acoustic interaction. This rotational motion "tags" the species and allows the acoustic wave applied by transducer 14 and having a frequency corresponding to this rate of gyration to sweep this tagged species toward the opposite end 12b of the sample container for removal as discussed above. The acoustic wave applied at this frequency will interact only with the spinning species to be separated.

By utilizing the respective acoustic properties of various species located in a mixture, the present invention permits a species separation on the basis of physical properties which have not been previously exploited for this purpose. These additional tagging characteristics allow one to separate complex mixtures which conventional methods could not.

Although particular embodiments of the invention have been described and illustrated herein, it is recognized that modifications and variations may readily occur to those skilled in the art and consequently it is intended that the claims be interpreted to cover such modifications and equivalents.

What is claimed as new and desired to be secured by Letters Patent of the United States is:

1. A method for separation of particulates in a liquid medium comprising the steps of:
    filling a sample container with the liquid medium containing various sizes of particulates to be separated;
    applying an acoustic wave having a particular frequency to the liquid medium in said sample container, whereby larger particulates are separated;
    removing the larger separated particulates from the sample container;
    increasing the frequency of the acoustic wave to separate smaller particulates; and
    removing the smaller separated particulates from the sample container.

* * * * *